(12) United States Patent
Ach et al.

(10) Patent No.: US 9,416,407 B2
(45) Date of Patent: Aug. 16, 2016

(54) METHOD FOR GENOME ANALYSIS (75) Inventors: Robert A. Ach, San Francisco, CA (US);
Carsten Carstens, San Diego, CA (US);
Bernd Buehler, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1375 days.

(21) Appl. No.: 12/243,571

(22) Filed: Oct. 1, 2008

(65) Prior Publication Data
US 2010/0081576 A1   Apr. 1, 2010

(51) Int. Cl.
*C12Q 1/68*   (2006.01)
(52) U.S. Cl.
CPC .................. *C12Q 1/6858* (2013.01)
(58) Field of Classification Search
CPC ........... C12Q 1/6858; C12Q 2533/101; C12Q 2537/143
USPC .................................... 435/91.2, 6
See application file for complete search history.

(56) References Cited

U.S. PATENT DOCUMENTS

| 2002/0177141 | A1 | 11/2002 | Chee et al. | |
| 2003/0165946 | A1* | 9/2003 | Evans | 435/6 |
| 2006/0073511 | A1 | 4/2006 | Jones et al. | |
| 2009/0087839 | A1* | 4/2009 | Liu et al. | 435/6 |
| 2010/0055681 | A1* | 3/2010 | Yamada | 435/6 |

OTHER PUBLICATIONS

Flores, M., et al. Recurrent DNA inversion rearrangements in the human genome. PNAS. 2007, vol. 104, No. 15, pp. 6099-6106.

* cited by examiner

*Primary Examiner* — Cynthia B Wilder (57) ABSTRACT

A method of sample analysis is provided. In certain embodiments, the method may comprise: a) contacting under primer extension conditions a genomic sample comprising a test genome with a set of at least ten sequence-specific primers that are complementary to sites in only one strand of a reference chromosomal region, to produce primer extension products, and b) analyzing the primer extension products to identify a chromosomal rearrangement in the test genome.

11 Claims, 5 Drawing Sheets

METHOD FOR GENOME ANALYSIS

BACKGROUND

In recent years, analysis of variation within the human genome has become a topic of interest in genomics. Single-Nucleotide Polymorphisms (SNPs) were the first type of sequence variation to be widely studied, and many such polymorphisms have been linked to human diseases. Interest in Copy Number Variants (CNVs) has grown in the past couple of years, with the realization that this type of genomic variation is much more commonplace than initially assumed. Chromosomal rearrangements are a third type of genomic variation, which have been much less studied than the other two.

This disclosure describes a method for detecting a chromosomal inversion or translocation and a kit for practicing the same.

SUMMARY

A method of sample analysis is provided. In certain embodiments, the method may comprise: a) contacting under primer extension conditions a genomic sample comprising a test genome with a set of at least ten sequence-specific primers that are complementary to sites in only one strand of a reference chromosomal region, to produce primer extension products, and b) analyzing the primer extension products to identify a chromosomal rearrangement in the test genome. In certain embodiments, the primer extension products may be analyzed by hybridization to an array. In other embodiments, the primer extension products may be analyzed by polymerase chain reaction. Kits for practicing the method are also provided.

BRIEF DESCRIPTION OF THE FIGURES

FIGS. 3A, 3B and 3C present the results of an experiment in which primer extension is performed on one DNA strand. Subtracted background signal is graphed against nucleotide position along a chromosomal segment. Filled circles represent probes from one strand, while open circles are probes from the opposite strand. The small open triangle represents the sequence used as the primer. The black arrow indicates the direction of the extension reaction. All the primers specifically yielded labeled products from only one strand. In panels A, B, and C, the detectable products ranged from about 6,000-13,000 bases long. Panel A, primer sequence is 85,286,764 and length of extension product is ~11,083 kb. Panel B, primer sequence is 85,328,920 and length of extension product is 6,929 kb. Panel C, primer sequence is 85,533,041 and length of extension product is 13,109 kb.

DEFINITIONS

The term "sample" as used herein relates to a material or mixture of materials, typically, although not necessarily, in liquid form, containing one or more analytes of interest.

The term "genomic sample" as used herein relates to a material or mixture of materials, containing genetic material from an organism. The term "genomic DNA" as used herein refers to deoxyribonucleic acids that are obtained from an organism. The terms "genomic sample" and "genomic DNA" encompass genetic material that may have undergone amplification, purification, or fragmentation. The term "test genome," as used herein refers to genomic DNA that is of interest in a study.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide" as used herein denotes a single stranded multimer of nucleotide of from about 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide that has a nucleotide sequence that is complementary to a region of a target nucleic acid. A primer binds to the complementary region and is extended, using the target nucleic acid as the template, under primer extension conditions. A primer may be in the range of about 20 to about 60 nucleotides although primers outside of this length are envisioned.

The term "primer extension conditions" as used herein refers to conditions suitable for the extension of a primer that is bound to a complementary region in a target nucleic acid. Primer extension conditions include incubating a duplex nucleic acid with nucleotides, a polymerase and a buffer for a period of time at a certain temperature. Such conditions are well known in the art. The resulting new strand produced by primer extension is referred herein as a "primer extension product."

The term "amplifying" as used herein refers to generating one or more copies of a target nucleic acid, using the target nucleic acid as a template.

The term "sequence-specific primer" as used herein refers to a primer that only binds to and extends at a single site in a haploid genome. In certain embodiments, a "sequence-specific" oligonucleotide may hybridize to a complementary nucleotide sequence that is unique in a sample under study.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional or substantially two-dimensional (as well as a three-dimensional) arrangement of addressable regions, e.g., spatially addressable regions or optically addressable regions, bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or calculated using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10).

As used herein, the term "$T_m$-matched" refers to a plurality of nucleic acid duplexes having $T_m$s that are within a defined range, e.g. ±5° C., ±10° C., or ±15° C.

The term "low-stringency hybridization conditions" as used herein refers to hybridization conditions that are suitable for hybridization of an oligonucleotide and a probe oligonucleotide that has a region that is complementary to the oligonucleotide. Such conditions may differ from one experiment to the next depending on the length and the nucleotide content of the complementary region. In certain cases, the temperature for low-stringency hybridization is 5°-10° C. lower than the calculated $T_m$ of the resulting duplex under the conditions used.

As used herein "high-stringency wash conditions" refers to wash conditions that provide for dissociation of duplexes that are nonspecifically hybridized that contains insufficient complementarity, but not dissociation of duplexes with insufficient complementarity. Such conditions release primer extension products that are not nonspecifically attached to the probe features on an array but do not release primer extension products specifically hybridized to a probe. Again, such conditions may differ from one experiment to the next depending on the length and the nucleotide content of the complementary region. In certain cases, the temperature for a high stringency wash may be 5°-10° C. lower than the calculated $T_m$ of a correctly hybridized duplex.

The term "chromosomal region" as used herein denotes a contiguous length of nucleotides in a genome of an organism. A chromosomal region may be in the range of 10 kb in length to an entire chromosome, e.g., 100 kb to 10 MB for example.

The term "reference chromosomal region," as used herein refers to a chromosomal region of known nucleotide sequence, e.g. a chromosomal region whose sequence is deposited at NCBI's Genbank database or other database, for example.

The term "strand" as used herein refers to a nucleic acid made up of nucleotides covalently linked together by phosphodiester bonds. One strand of nucleic acid does not include base-pairing nucleotides that are associated solely through hydrogen bonding, although that strand may be base-paired with a complementary strand via hydrogen bonding.

The nucleic acid of a chromosomal region exists in a double-stranded form, and as such, has two complementary strands of nucleic acid referred to herein as the "first" and "second" strands. In certain cases, complementary strands of a chromosomal region may be referred to as "plus" and "minus" strands, the "top" and "bottom" strands or the "sense" and "antisense" strands. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example. The second strand of a region is complementary to that region.

The term "first strand," as used herein, refers to either strand of a nucleic acid but not both strands of a nucleic acid. When an oligonucleotide or a primer binds or anneals "only to a first strand," it binds to only one strand but not the other. The term "second strand," as used herein, refers to the strand that is complementary to the "first strand." When an oligonucleotide or a primer binds or anneals "only to a one strand," it binds to only one strand, e.g., the first or second strand, but not the other strand.

The term "complementary to sites in only a first strand," as used herein, refers to complementarity to sites only on a first strand but not a second strand of a reference nucleic acid.

The term "chromosomal rearrangement," as used herein, refers to an event where one or more parts of a chromosome are rearranged within a single chromosome or between chromosomes. In certain cases, a chromosomal rearrangement may reflect an abnormality in chromosome structure. A chromosomal rearrangement may be an inversion, a deletion, an insertion or a translocation, for example.

The term "rearrangement junction" refers to a nucleotide sequence that contains the junction between two nucleic acid segments that have been rearranged relative to one another.

The term "inversion junction" is a nucleotide sequence that contains the junction between two nucleic acid segments, one of which has undergone chromosomal inversion. A chromosomal inversion is a chromosome rearrangement in which the orientation of a segment of a chromosome is reversed.

The term "translocation junction" is a nucleotide sequence that contains the junction between two nucleic acid segments, one of which has undergone chromosomal translocation. A chromosomal translocation is a rearrangement of parts between non-homologous chromosomes.

DESCRIPTION OF EXEMPLARY EMBODIMENTS

A method of sample analysis is provided. In certain embodiments, the method may comprise: a) contacting under primer extension conditions a genomic sample comprising a test genome with a set of at least ten sequence-specific primers that are complementary to sites in only one strand of a reference chromosomal region, to produce primer extension products, and b) analyzing the primer extension products to identify a chromosomal rearrangement in the test genome.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

As noted above, certain embodiments of the method involve contacting a genomic sample containing a test genome with a set of sequence specific primers that are complementary to sites in only one strand of a reference chromosomal region, to produce primer extension products. The primer extension products are then analyzed to identify a chromosomal rearrangement.

Figure 1:
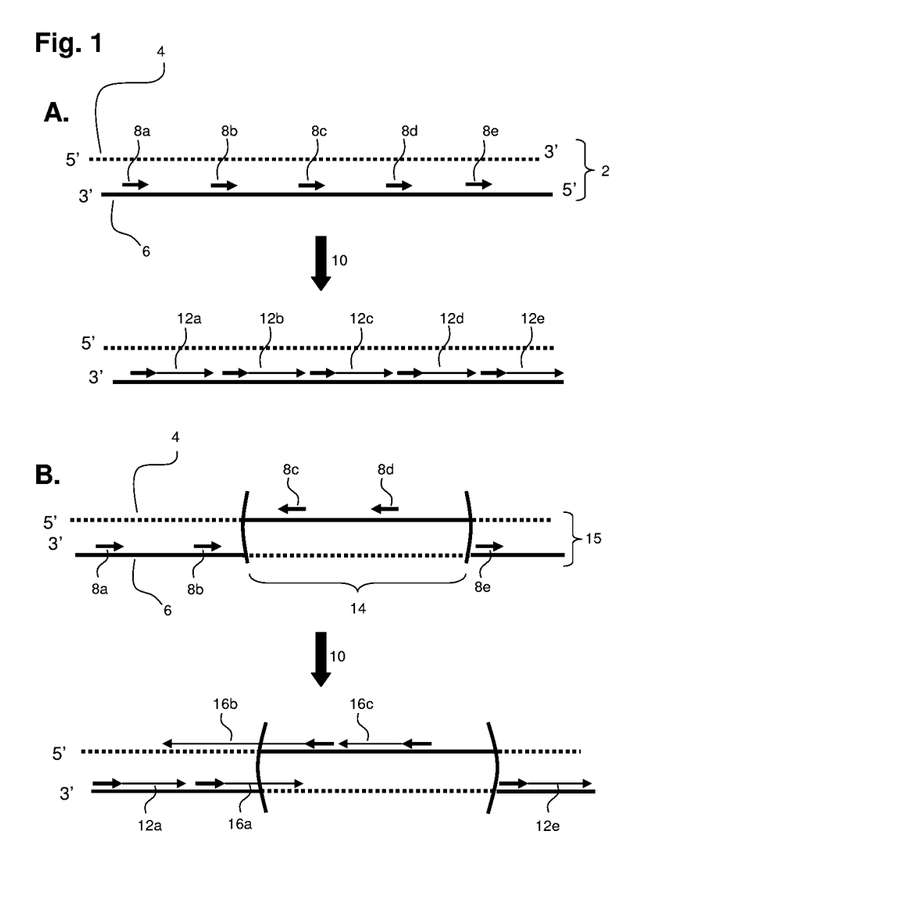
FIG. 1 schematically illustrates certain features in one embodiment of a method for sample analysis. As illustrated, this embodiment includes extending primers hybridized to a chromosomal region with (Panel B) or without (Panel A) a chromosomal inversion relative to a reference chromosomal region.

In the following description, the strand to which the primers anneal, i.e., the "one strand", is arbitrarily designated as the second strand to be consistent with FIG. 1, where the first strand is the top strand, and the second strand is the bottom strand. Since this naming system is arbitrary, the names assigned to the strands could be reversed (i.e., the strand to which the primers anneal could be designated as the first strand). Certain features of the subject method are illustrated in FIG. 1. With reference to FIG. 1, certain embodiments of the method include contacting a genomic sample, e.g. a sample containing a test genome 2, with sequence-specific primers 8 under primer extension conditions 10 to produce primer extension products. The primers are designed to anneal to only one strand of a reference chromosomal region, where a reference chromosomal region has a known nucleotide sequence and is from the same species as the test genome.

The primer extension products are then analyzed, e.g., using an array or by polymerase chain reaction, to identify primer extension products that indicate that a chromosomal rearrangement has occurred in the test genome relative to the reference chromosomal region. Such primer extension products contain: a) a first segment that is complementary to the second strand of the reference chromosomal region, and b) a second segment that is not complementary to the second strand of the reference chromosomal region. The junction between the two segments corresponds to a junction of a chromosomal rearrangement. In certain cases and as will be discussed in greater detail below, the second segment may be complementary to the first strand of the reference chromosomal region, in which case the test genome contains an inversion relative to the reference chromosomal region. In other cases, the second segment may be complementary to a region of a different chromosome, in which case the test genome contains a translocation. As such, in certain cases a primer extension product may contain non-contiguous segments in the reference chromosomal region, indicating that a rearrangement has occurred.

FIG. 1A illustrates method in which no chromosomal rearrangement is identified. As illustrated in FIG. 1A, the plurality of primers 8 anneal to sites spaced across strand 6 of a chromosomal region of the test genome and none of the primers bind to strand 4. The primers are then extended 10 using strand 6 as the template to produce a plurality of primer extension products 12a-12e. As shown in FIG. 1A, the entire length of each of the primer extension products is complementary to strand 6 and, as such, is the same as that expected for the reference chromosomal region. In this case, there is no rearrangement in the chromosomal region of the test genome relative to the reference chromosomal region.

In other embodiments, a test genome may contain one or more chromosomal rearrangements that can be identified by analyzing the primer extension products. FIG. 1B illustrates method in which the test genome contains an inverted segment 14 in the chromosomal region. When a plurality of primers designed to anneal only to a second strand 6 of the reference chromosomal region are hybridized with a chromosomal region containing an inverted segment, primers that anneal to sites in the inverted segment 14 bind to the other strand because of the inversion.

In the example shown in FIG. 1B, primers 8a, 8b, and 8e anneal to the second strand 6, while primers 8c and 8d anneal to the first strand 4. After primer extension, some primer extension products (e.g. 12a, 12e, and 16c) may be of the same nucleotide sequence as those that would be produced if the chromosomal region of the test genome is the same as the reference chromosomal region. However, in this case, some primer extension products, e.g., product 16b, are different from those that would be produced using the reference chromosomal region because they cross an inversion junction. These different primer extension products contain two segments: a first segment produced using the second strand as a template, and a second segment not produced using the second strand as a template. The second segment contains a nucleotide sequence different to that which would be produced if the test genome does not contain an inversion, relative to the reference chromosomal region. As shown in FIG. 1B, a primer extension product containing a nucleotide sequence of a junction of a chromosomal inversion includes both a sequence of the first strand of the reference chromosomal region (e.g. strand 4) in addition to a sequence of the second strand of the reference chromosomal region (e.g. a sequence of strand 6).

Primer extension products produced using a test genome containing an inversion may be detected using a nucleic acid array (e.g. an array containing probes that bind to the first strand of the reference chromosomal region), or by polymerase chain reaction, for example.

Similar methodology may be used to detect a translocation in a chromosomal region. In this case, primers designed to bind to only a second strand of a reference chromosomal region are annealed to a region containing a translocation. Certain of those primers will be extended through the translocation junction and, as such, one or more of the resultant primer extension products contains a first segment complementary to the second strand of a reference chromosomal region and a second region complementary to a different chromosome. As described previously, this primer extension product contains a nucleotide sequence that contains the nucleotide sequence of non-contiguous segments of a reference genome.

Primer extension products produced using a test genome containing a translocation may also be detected using a nucleic acid array (e.g. an array containing probes that bind to other chromosomal regions other than the reference chromosomal region), or by polymerase chain reaction, for example.

As noted above, the method includes analyzing the primer extension products to identify a chromosomal rearrangement. The primer extension products may be analyzed by a variety of different techniques. In one embodiment, they may be analyzed by: i) contacting the primer extension products with an array of probes under hybridization conditions to produce a contacted array; and ii) reading the contacted array to detect a chromosomal rearrangement. In certain cases, primer extension products are labeled with a label, where the label is used to detect the presence of any primer extension product hybridized to the array. In certain embodiments, the array is addressable such that detection of a signal, such as a fluorescent signal, in a specific location on the array identifies at least the partial nucleotide sequence of the hybridized primer extension product in that location.

In particular embodiments, an array may contain one or more second probes that are complementary to sites of the second strand of the reference chromosomal region. Binding of primer extension products made using a test genome and primers complementary to only the second strand of a reference chromosomal region to the second probes indicates that a primer extension product comprises an inversion junction. With reference to FIGS. 1A and 1B, in order to differentiate between a chromosomal region that contains an inversion junction and a chromosomal region that does not, the second probes contain sequences complementary to sites in strand 6. The primer extension products shown in FIG. 1A do not bind to second probes because all primer extension products 12 are complementary to sites in strand 6 However, when a primer extension product contains an inversion junction such as primer extension product 16b in FIG. 1B, it binds to probes complementary to strand 6 because it contains a sequence complementary to strand 4. The array may further comprise probes that are complementary to strand 4 as positive control probes. Analysis of the array can reveal that the test genome contains an inversion as well as the chromosomal inversion junction.

In other embodiments, an array may comprise one or more translocation probes that are complementary to sites in a second chromosomal region that is different to the reference chromosomal region, e.g., on a different chromosome, such that binding of a primer extension product to the translocation probes indicates that the primer extension product comprises a translocation junction. In certain cases, the probes on the array are complementary to a region of a different chromosome in the genome to which the primers do not bind. When there is a translocated segment in the chromosome, one or more primer extension products may contain sequences of the translocated segment. Binding of the primer extension product to the translocation probe may indicate the sequence of the translocated segment and the chromosome number from which the translocated segment derives. Referencing FIG. 1, a positive control probe for a target chromosome without any translocation may contain sequences complementary to strand 4 of the target chromosome. Conversely, a negative control probe or test probes may contain sequences complementary to chromosomes other than the target chromosome.

Figure 2:
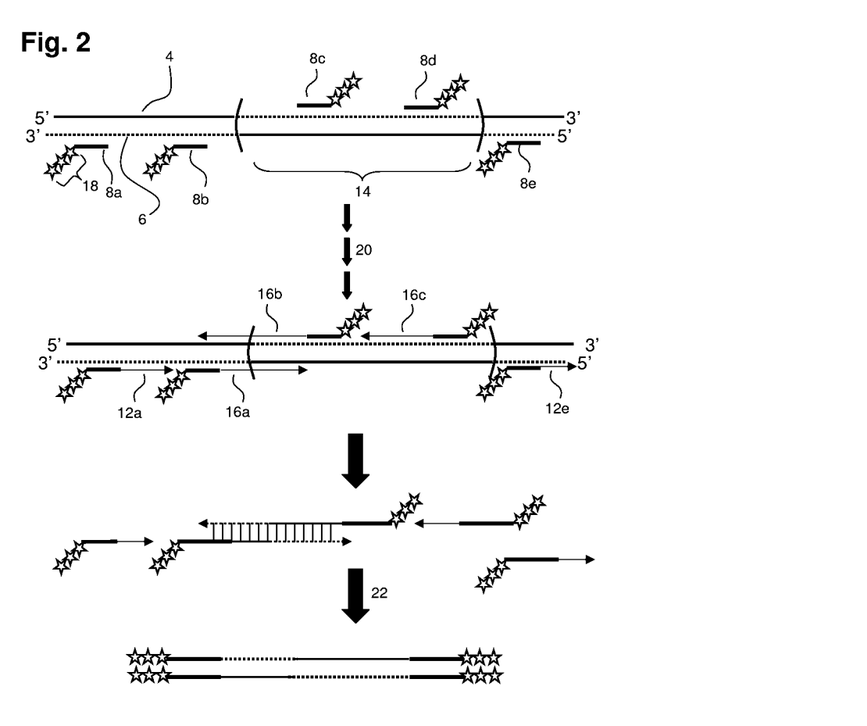
FIG. 2 schematically illustrates certain features of another embodiment of a method for sample analysis described herein.

In alternative embodiments, the method may involve amplifying the primer extension products to produce amplified extension products. In certain cases, the method also comprises detecting the amplified extension products. Certain features of these embodiments are illustrated in FIG. 2 and are described in greater detail below. Generally, a plurality of strand-specific primers is contacted with a genomic sample containing a test genome. As shown in FIG. 2, the primers 8 are predicted to bind to the bottom strand 6 and have a 5' sequence tag 18, i.e., a sequence of nucleotides that is known and the same in the different primers. If the chromosome has an inverted segment 14, certain primers 8c and 8d, may bind to the top strand 4. Then, multiple rounds of primer extension 20, each of which includes primer extension, denaturing, and reannealing, may be performed with or without incorporating labeled or modified nucleotides. Next, the primer extension products are used as a substrate in a polymerase chain reaction (PCR) 22 using a primer that is part of the tag sequence 18. As shown in FIG. 2, PCR products are only obtained if there is an inverted segment. If there are no inverted segments, no PCR products are obtained. The amplified product may be detected by, e.g., running the amplification reaction mixture in a gel or over a column. In certain cases, detecting may comprise parallel-sequencing a plurality of amplified products.

In addition to determining if a chromosomal inversion or translocation has occurred, array hybridization and amplification assays can also be employed to map the location of the rearrangement. In methods in which an array is employed, information on which probes hybridize and which probes do not hybridize can be mapped onto the sequence of a genome and, as such, the rearrangement junction can be mapped to between two probe binding sites. In order to achieve high resolution map of a chromosomal arrangement, a higher density of primers and/or probes may be used. If higher resolution or further verification is desired, the process of designing primers that anneal at higher density, performing PCR, and analyzing PCR products may be an iterative process. The techniques involved in these and other embodiments to map a chromosomal rearrangement are routine and well within the knowledge of one of skilled in the art. In other embodiment, the nucleotide sequence and the location of the rearrangement may be accomplished by PCR using primers designed to specifically anneal to the sub-region of the test chromosomal region suspected to contain the rearrangement. PCR products produced using those primers can be sequenced.

In certain embodiments, the method may include contacting a genomic sample with a set of at least 2, at least 5, at least 10, at least 100, at least 1000, up to 10,000, up to 50,000 or up to 100,000, or up to 1,000,000 or more sequence specific primers. The primers may have an average length of about 10 to about 100 bases, about 10 to about 80 bases, about 10 to about 50 bases, or about 10 to about 30 bases. In particular embodiments, a primer is an oligonucleotide of 30 to 60 bases in length. The primers used in the subject methods may be $T_m$-matched.

The primers are sequence specific such that each of the plurality of primers may anneal to a specific site, all of which are on one strand of a target chromosome. In certain cases, the primers anneal to sites spaced across all chromosome regions in a genome such that after primer extension, the primer extension products contain sequences that reflect the entire genome. The sites to which the primers anneal may be spaced apart by a number of bases less than the length of the predicted primer extension product. In certain cases, each of the plurality of annealed primers is spaced apart from the adjacent annealed primer by an average of about 1,000 to 100,000 bases or more, e.g., 2000 to 75,000 bases, 3,000 to 50,000 bases, or 5,000 to 10,000 bases, for example.

As discussed previously, the subject method employs sequence-specific primers that bind to sites on only one strand of a reference chromosomal region. Since the genome sequences of many organisms, including many bacteria, fungi, plants and animals, e.g., mammals such as human, primates, and rodents such as mouse and rat, are known and some are publicly available (e.g., in NCBI's Genbank database), the design of such primers is well within the skill of one of skilled in the art. In certain cases, the reference genomes contain wild-type alleles with respect to a genetic disease and/or mutation under study.

In certain cases, multiple sets of a plurality of primers may be employed by the subject method where each set is specific for a single reference chromosomal region. Multiple chromosomal regions, e.g., several chromosomes or an entire genome, can be analyzed using such multiple sets of primers.

The subject method may use primers that are labeled or unlabeled. The primers may be labeled using labeled nucleotides. In certain embodiments, the primers may contain biotinylated nucleotides. In other embodiments, the primer may contain a dye, e.g. Cy3. The primers may contain unstructured nucleic acids (UNA). Methods of making and using UNAs are known in the art, as taught by U.S. Pat. No. 7,371,580, the disclosure of which is incorporated herein by reference. In certain embodiments, unstructured nucleic acids inhibit primer-dimer formation and raise the $T_m$ of the hybridized primer to genomic DNA.

In certain embodiments, the subject method contacts a set of primers with a genomic sample. In one embodiment, the genomic sample may contain genomic DNA from a mammal, such as a human or a mouse. The genomic sample may be crude so to contain additional cellular material other than genomic DNA. In other cases, the genomic sample may have undergone purification. The genomic sample may contain genomic DNA which has been amplified or not amplified. The genomic DNA in the genomic sample may or may not be fragmented. In certain cases, the genomic DNA is relatively intact, with an average size of greater than 10,000, 100,000, or 1 million bases.

In certain embodiments, the primer extension conditions comprise contacting a plurality of primers to a reagent mix comprising nucleotides. As noted previously, the nucleotides may be labeled or unlabeled. The reagent mix may comprise of a thermostable polymerase. In alternative embodiments, the polymerase employed in the subject method has high processivity and strand-displacement activity. High processivity allows for long primer extension products.

The polymerase used in the extension reaction may include but is not limited to any DNA-template dependent DNA polymerase, such as a template-dependent polymerase (e.g., T4 DNA polymerase, Taq polymerase, reverse transcriptase (MMLV RT), the Klenow fragment of DNA polymerase I and the like), thermostable template-dependent polymerases (such as Pfu), or any combination thereof. As would be recognized by one of skill in the art, a wide variety of DNA polymerases employable in the subject methods are available.

In one embodiment, the polymerase may be Pfu-fusion Exo (−), which is the exonuclease-deficient version of Pfu polymerase fused to a double-stranded DNA-binding domain. In certain cases, a Pfu clamp loader may be added to the reagent mix to increase the processivity of the polymerase.

In certain cases, the primer extension conditions comprise primer annealing and polymerization at high temperature, which may avoid false priming. In another embodiment, the polymerase may be added after the primers are annealed to ensure that polymerization occurs only after annealing is complete. Polymerase may also be kept inactive in the same reaction vessel of the primer extension condition by photocaging either the polymerase or the primers.

The primer extension products may be labeled or unlabeled. In the case of labeled primer extension products, the label may be incorporated as labeled nucleotides during polymerization. In an alternative embodiment, the primers themselves may already be labeled. In certain cases, the primer extension products may be labeled post-transcriptionally. For example, the primer extension products may contain biotinylated nucleotides, nucleotides with linkers or modified nucleotides, which can be conjugated with a detectable moiety after polymerization In certain embodiments, the primer extension products may be analyzed immediately after primer extension reaction, without a purification or concentration step. In other embodiments, the method provides for removal of the test genomic DNA before the primer extension products are analyzed. Removal of the genomic DNA may be done using, for example, phosphorylated genomic DNA and nonphosphorylated primers. In certain cases, the genomic DNA may be phosphorylated before contacting the primers with the genomic sample to ensure that the genomic DNA is phosphorylated. After primer extension, genomic DNA may be removed with an exonuclease specific for phosphorylated DNA, e.g. Strandase, leaving the primer extension products intact for analysis. Genomic DNA may also be fragmented to aid in the exonuclease reaction. In another embodiment, incorporation of thio-nucleotides in the primer extension products may also aid in the specification of exonuclease to degrade only genomic DNA. If methylated cytosine is incorporated into the primer extension products, DNA methylase may be used to specifically biotinylate the genomic DNA using a biotinylation substrate on the unmethylated genomic DNA (Limasauskas et al. 2007). In another embodiment, the genomic DNA may be methylated first and the primer extension products may be labeled with a DNA methylase using a fluorescent substrate. Other methods to remove genomic DNA and to differentially label genomic DNA from the primer extension products are contemplated.

As noted above, method may comprise hybridizing to an array. In general, the array contains at specific locations a plurality of probes, each of which is an oligonucleotide. In certain embodiments, the probe may contain 10 to about 100 bases, about 10 to about 80 bases, about 30 to about 70 bases, or about 35 to about 50 bases in length. In particular embodiments, the subject features contain oligonucleotides are 20 to 60 bases in length.

In many embodiments, a subject array may contain features that correspond to (i.e., may be used to detect) a single chromosomal region or a plurality of different chromosomal regions (which may be on a single chromosome or different chromosomes) of a cell.

In certain embodiments, a subject array contains a plurality of probe features that correspond to a plurality of chromosomal regions. Accordingly, a subject array may have oligonucleotide features that correspond to 1, more than about 5, more than about 10, more than about 15, more than about 20, more than about 25, more than about 30, more than about 35, more than about 40, more than about 50, or more than about 60, up to 100 or more chromosomal regions, or up to and including most or all of the genome.

Further, the subject arrays may contain a plurality of oligonucleotide features for a particular chromosome. For example, the subject arrays may contain at least 100 or more, about 1,000 or more, usually up to about 10,000 or 100,000 or more, oligonucleotide features (i.e. features containing oligonucleotides of different sequence) for each chromosomal region interest. An array that contains probe features to scan primer extension products that cover the whole genome may contain at least 100,000, 300,000, or 500,000 or 1,000,000 or more probe features.

In many embodiments, the array probes employed in the subject method have been designed and arranged on a solid, planar substrate according to one or more particular parameters to be suitable for use in a given application, where representative parameter include, but are not limited to: length, melting temperature ($T_m$), non-homology with other regions of the genome, signal intensities, kinetic properties under hybridization conditions, etc., see e.g., U.S. Pat. No. 6,251,588, the disclosure of which is herein incorporated by reference. In certain embodiments, the entire length of the subject probe is employed in hybridizing to primer extension products, while in other embodiments, only a portion of the subject probe has sequence that hybridizes to sequence found in the primer extension product, e.g., where a portion of the oligonucleotide serves as a tether or stacking stability. In certain cases, a plurality of array probes is $T_m$-matched such that when hybridized to their corresponding targets may have similar $T_m$.

In other embodiments, the probes are complementary to only one strand of a target chromosome, as described previously. On certain arrays, the second probes are complementary to sites on the second (or bottom) strand of the target chromosome, containing sites to which the strand-specific primers are complementary. In some embodiments array may have both second probes and probes that are complementary to sites on the top strand as a positive control probes.

In general, methods for the preparation of polynucleotide arrays are well known in the art (see, e.g., Harrington et al, Curr. Opin. Microbiol. (2000) 3:285-91, and Lipshutz et al., Nat. Genet. (1999) 21:20-4) and need not be described in any great detail. The subject oligonucleotide arrays can be fabricated using any means, including drop deposition from pulse jets or from fluid-filled tips, etc, or using photolithographic means. Either polynucleotide precursor units (such as nucleotide monomers), in the case of in situ fabrication, or previously synthesized polynucleotides can be deposited. In some embodiments, the arrays may be constructed to include oligonucleotide analogs such as nucleotide analogs such as 2,6-aminopurines. Such methods are described in detail in, for example U.S. Pat. Nos. 6,242,266, 6,232,072, 6,180,351, 6,171,797, 6,323,043, and U.S. Patent Application US20040086880 A1, etc., the disclosures of which are herein incorporated by reference.

Conditions for array hybridization are generally known. Generally, the stringency of the wash conditions determines whether a nucleic acid is specifically hybridized to a probe. The stringency may be low or high depending on the $T_m$ of the expected duplexes to form between the primer extension products and the oligonucleotide probe on the array. Some exemplary conditions are as follows. Wash conditions may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook (cited above), Ausubel, et al., Short Protocols in Molecular Biology, 3rd ed., Wiley & Sons 1995, or Tijssen, Hybridization with Nucleic Acid Probes, Parts I and II (Elsevier, Amsterdam 1993) for detailed descriptions of equivalent hybridization and wash conditions and for reagents and buffers, e.g., SSC buffers and equivalent reagents and conditions.

A specific example of stringent assay conditions is rotating hybridization at 65° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Kits

Also provided by the subject invention are kits for practicing the subject method, as described above. The subject kit contains a set of at least 10, at least 1,000, at least 10,000, or at least 100,000 or more sequence-specific primers that are complementary to sites in only one strand of a reference chromosomal region. In certain kits, the primers may be specific to only one strand of one reference chromosome or a plurality of reference chromosomes. The kit may further contain a polymerase, reagents for polymerization (e.g., a buffer, nucleotides, etc), materials for fluorescent labeling of polymerase products, and a reference sample to be employed in the subject method.

In additional embodiments, the kit further comprises an array of probes that are complementary to sites of a second strand of the chromosomal region. The kit may also comprise probes that are complementary to sites of a second strand of a plurality of reference chromosomal regions. In an alternative embodiment, the kit further comprises an array of probes predicted to be complementary to sequences of a chromosomal region different from the reference chromosomal region whose sites the primers are predicted to anneal to. The kit may provide additional probe features on the array for positive and negative controls, depending on the analysis.

The kits may be identified by the type of primers included and the chromosomal regions the primers are predicted to bind to. The kits may be further identified by the method of analyzing the primer extension products.

In addition to above-mentioned components, the subject kit typically further includes instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control analyte mixtures, e.g., two or more control analytes for use in testing the kit.

Utility

The subject method finds use in a variety of applications, where such applications generally include genomic DNA analysis applications in which the presence of a particular chromosomal inversion or translocation in a given sample is detected. In general, the method involves the use of a set of primers designed to anneal to only one strand of a target chromosome or chromosomal region. After primer extension, the primer extension products are analyzed.

Briefly, the genomic sample containing a test genome suspected of containing a chromosomal rearrangement is contacted with strand-specific primers under primer extension conditions. The primer extension products are then analyzed by hybridizing to an array or amplified for other methods of analysis, as described above.

Specific analyte detection applications of interest include but are not limited to chromosomal rearrangements. One embodiment of the genomic analysis assay allows the detection of a chromosome inversion. In this embodiment, the assay contacts primers specific for only a second strand of a reference chromosomal region under primer extension conditions and hybridizes the primer extension products to probes complementary to the second strand, named second probes. If the test chromosomal region contains an inverted segment, one or more primer extension products may hybridize to the probes to yield a positive signal. Linking the location of the probe on an addressable array to a database may provide the nucleotide sequence information of the primer extension product hybridized to the second probe. Using the sequence information, the location of the inversion junction may be deciphered.

The subject method also finds utility in the detection of chromosomal translocation. In this embodiment, array probes used to detect primer extension products contain sequences not found in the target chromosomal region. These probes may be called translocation probes. If a segment of a different chromosome has translocated to the target chromosome, one or more primer extension products may contain sequences complementary to the translocated segment. Hybridization of the primer extension products to translocation probes indicates a translocation event. Similarly, linking the location of the probe on an addressable array to a database may provide the nucleotide sequence information of the primer extension product hybridized to the translocation probe. Using the sequence information, the location of the translocation junction may be deciphered.

The subject method finds use in a variety of diagnostic and research purposes since chromosomal inversions and translocations play an important role in conditions relevant to human diseases and genomic evolution of many organisms.

In particular, the above-described methods may be employed to diagnose, or investigate cancerous condition or other mammalian diseases, including but not limited to, leukemia, breast carcinoma, prostate cancer, Alzheimer's disease, Parkinsons's disease, epilepsy, amyotrophic lateral sclerosis, multiple sclerosis, stroke, autism, mental retardation, and developmental disorders. The disease may be genetically inherited or sporadic. Many exemplary chromosomal rearrangements discussed herein are associated with and are thought to be a factor in producing these disorders. Knowing the type and the location of the chromosomal rearrangement may greatly aid the diagnosis, prognosis, and understanding of various mammalian diseases.

To apply the subject method for one or more of the above-mentioned utilities, a cellular sample may be obtained from a subject and the sample tested using the methods described above. In certain embodiments, the sample may be compared with a reference. The reference may be a genomic sample from a supposedly healthy or wild-type organism. Briefly, the method comprises contacting under primer extension condition the test genome with a plurality of strand-specific primers and contacting under primer extension condition a reference genome with the same plurality of strand-specific primers. After primer extension, the primer extension products from the test sample are compared against those of the reference. One of the many ways to compare the two samples is to hybridize the primer extension products from the test sample and from the reference to separate arrays of second probes.

For example, based on a positive signal on an array feature, the test sample may be found to contain an inverted segment on chromosome 19. Since the reference presumably has a wild-type chromosome 19, there may be no signal beyond background when the reference primer extension products are contacted with the probe feature at which the test sample yields a positive result. In another embodiment, the test sample is from an organism suspected to have cancer and the reference samples may comprise of a negative control (non-cancerous) representing wild-type genomes and second test sample (or a positive control) representing a cancer associated with a known chromosomal rearrangement. In this embodiment, comparison of all these samples with each other using the subject method may reveal not only if the test sample yields a result that is different from the wild-type genome but also if the test sample may have the same or similar genomic rearrangements as another cancer test sample.

Other assays of interest which may be practiced using the subject method include: genotyping, scanning of known and unknown mutation, gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

The above described applications are merely representations of the numerous different applications for which the subject array and method of use are suited. In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

In certain embodiments of the subject methods in an array, the array may typically be read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER device available from Agilent Technologies, Santa Clara, Calif. Other suitable apparatus and methods are described in U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934; the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

EXAMPLE

An experiment was performed to test whether primers may be extended from genomic DNA to label only one DNA strand. 2 µg of human male genomic DNA was incubated with a mixture of 18 primers specific for regions on one strand of the X chromosome. The primers were present at a 10,000× molar excess over the genomic target. Primers and genomic DNA were annealed at 67° C. for 44 hours, after an initial denaturation at 95° C. for 3 minutes. Primers were then extended with Exo(−) Pfu polymerase/Sso7 DNA-binding domain fusion in 200 µM dATP, dGTP, dCTP, 40 µM dTTP and 60 µM Cy3-dUTP at 67° C. for 3 minutes before heating the block to 72° C. and incubating for 90 minutes. Following column cleanup, samples were hybridized to a DNA microarray (Agilent Technologies) containing 60 mer probes for both strands of the targeted X chromosome regions. Array hybridization and washing conditions were performed according to the manufacturer's protocol (Agilent Technologies). Microarray results were extracted using Agilent Feature Extraction software (v9.5.3.1).

Figure 3A:
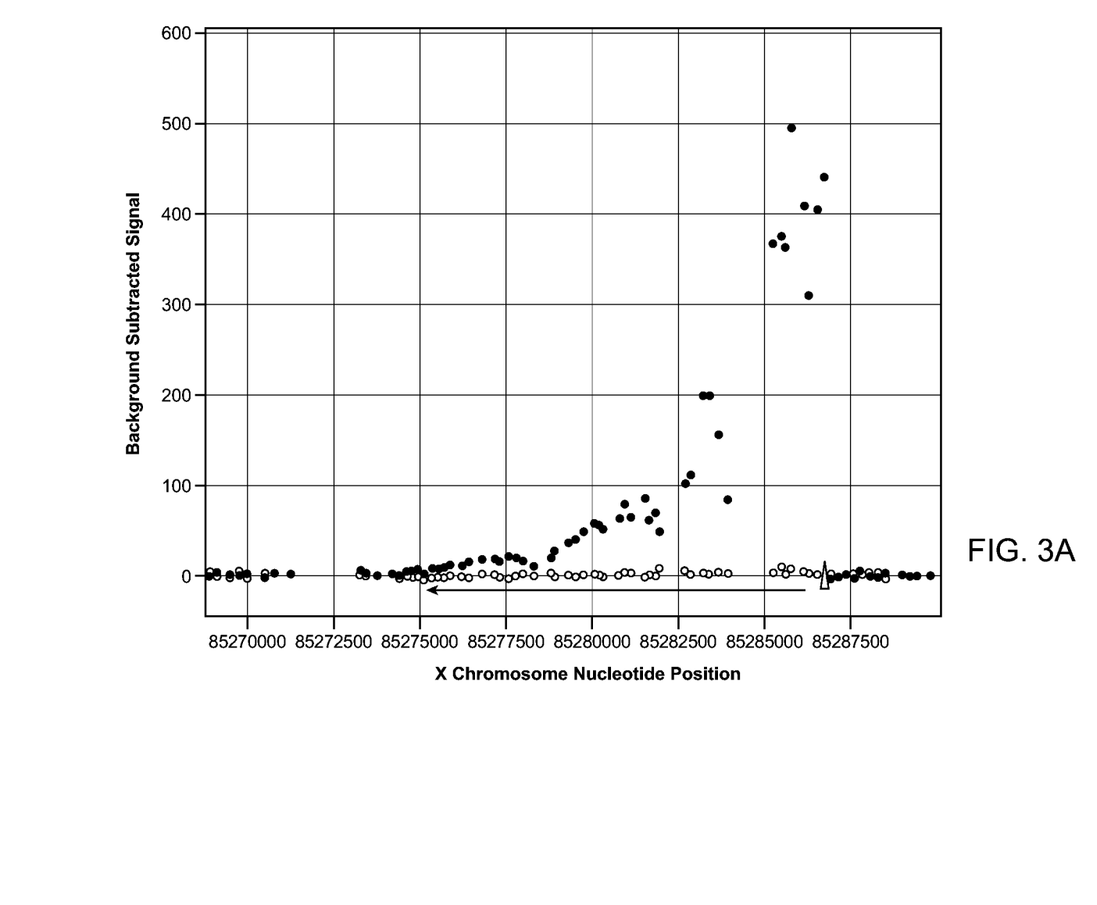
Figure 3B:
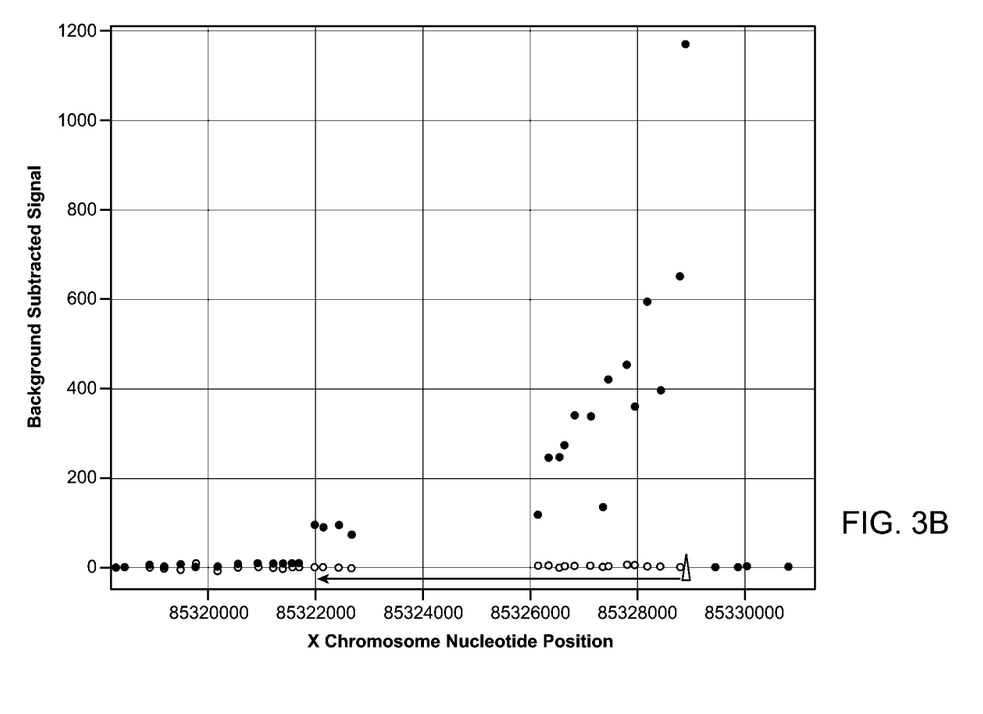
Figure 3C:
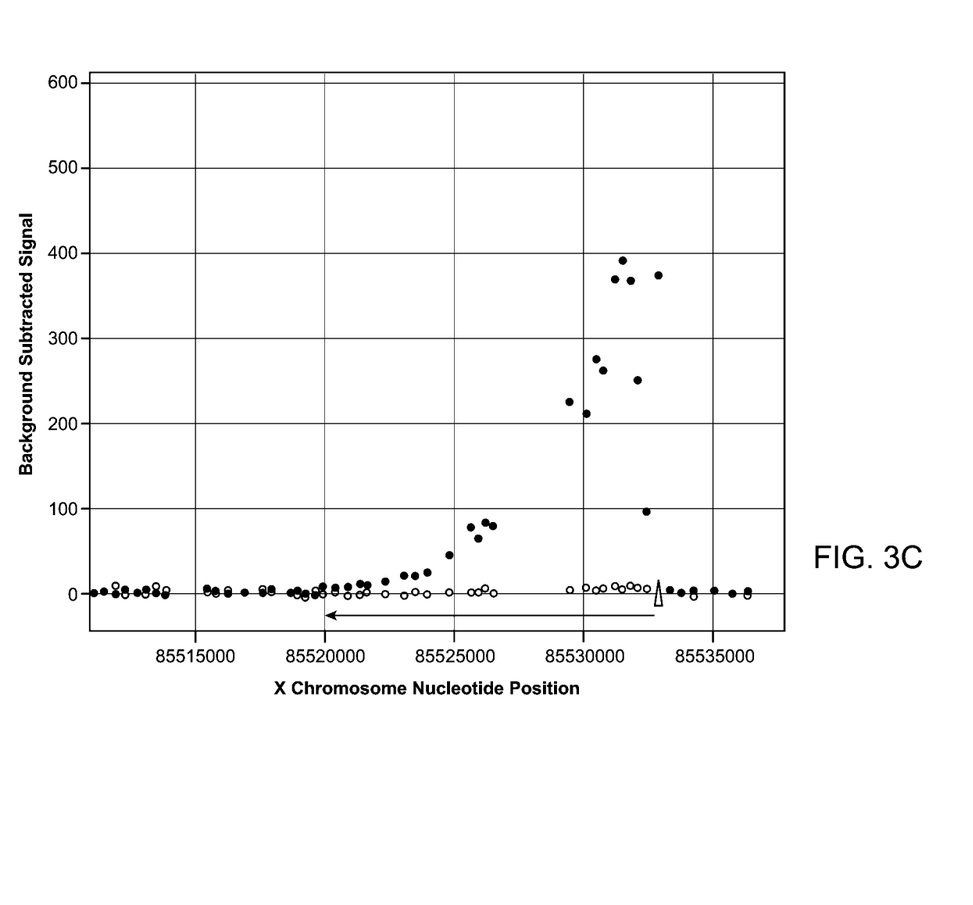

Analysis of the data showed specific extension from all the primers from only one stand of the X chromosome. Examples of the results are shown in FIGS. 3A, 3B and 3C. The plots show the position of the microarray probes on the x axis, and the background-subtracted hybridization signals on the y axis. Filled circles represent probes from one strand, while open circles are probe from the opposite strand. The small open triangle represents the sequence used as the primer. The black arrow indicates the direction of the extension reaction. All the primers specifically yielded labeled products from only one strand. In FIG. 3, the detectable products ranged from about 6,000-13,000 bases long.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of analyzing a test genome, comprising:
    a) contacting under primer extension conditions a genomic sample comprising said test genome with a set of at least 10 sequence-specific primers that are complementary to sites in only a top strand strand of a reference chromosomal region from the same species as said test genome, to produce primer extension products; and
    b) hybridizing said primer extension products to an array of probes comprising:
        i. first probes that are complementary to the top strand of said reference chromosomal region and
        ii. second probes that are complementary to the bottom strand of said reference chromosomal region;
    to obtain hybridization results; and
    c) analyzing said hybridization results to identify a chromosomal inversion or translocation in said test genome.

2. The method of claim 1, wherein binding of said primer extension products to said first probes indicates that said test genome comprises an inversion.

3. The method of claim 1, wherein said array comprises translocation probes that are complementary to sites in a chromosomal region from a different chromosome, wherein binding of said primer extension product to said translocation probes indicates that said test genome comprises a translocation.

4. The method of claim 1, wherein said primers bind to sites that are spaced across said reference chromosomal region.

5. The method of claim 1, wherein said primers are labeled.

6. The method of claim 1, wherein said primer extension conditions comprises contacting said plurality of primers to a reagent mix comprising labeled nucleotides.

7. The method of claim 1, wherein said method comprises removing said test genome from said genomic sample after said contacting step.

8. The method of claim 1, wherein said method further comprises:
    i) amplifying said primer extension products to produce amplified extension products; and
    ii) analyzing said amplification products.

9. The method of claim 1, wherein said species is a mammal.

10. A method comprising:
    a) analyzing a first test genome according to the method of claim 1;
    b) analyzing a second test genome according to the method of claim 1; and c) comparing results obtained from analyzing said first test genome to results obtained from analyzing said second test genome.

11. The method of claim 10, wherein said first test genome is from a cell that is cancerous and said second genomic sample is from a cell that is non-cancerous.

* * * * *